(12) United States Patent
Colling (10) Patent No.: US 11,760,400 B2
(45) Date of Patent: Sep. 19, 2023

(54) APPARATUS FOR SUSPENDING RADIO-OPAQUE CURTAINS

(71) Applicant: Timothy P. Colling, Farmington Hills, MI (US)

(72) Inventor: Timothy P. Colling, Farmington Hills, MI (US)

(*) Notice: Subject to any disclaimer, the term of this patent is extended or adjusted under 35 U.S.C. 154(b) by 325 days.

(21) Appl. No.: 17/120,369

(22) Filed: Dec. 14, 2020

(65) Prior Publication Data

US 2021/0179157 A1 Jun. 17, 2021

Related U.S. Application Data

(60) Provisional application No. 62/988,542, filed on Mar. 12, 2020, provisional application No. 62/947,635, filed on Dec. 13, 2019.

(51) Int. Cl.
| | |
|---|---|
| *B62B 3/04* | (2006.01) |
| *A47H 1/00* | (2006.01) |
| *F16M 13/02* | (2006.01) |

(52) U.S. Cl.
CPC ............ *B62B 3/04* (2013.01); *A47H 1/00* (2013.01); *F16M 13/02* (2013.01)

(58) Field of Classification Search
CPC .......... B62B 3/04; B62B 3/002; B62B 3/005; A47H 13/04; F16M 13/02; A01G 5/04; A47G 25/32; A47G 25/325
USPC ...................................... 280/47.35; 23/265 H
See application file for complete search history.

(56) References Cited

U.S. PATENT DOCUMENTS

| | | | | |
|---|---|---|---|---|
| 2,980,379 | A * | 4/1961 | Goldfus | F16B 47/00 248/312 |
| 5,421,548 | A * | 6/1995 | Bennett | A61G 12/008 5/503.1 |
| 5,556,065 | A * | 9/1996 | Wadley | A61M 5/1415 248/129 |
| 5,704,577 | A * | 1/1998 | Gordon | F16B 7/0493 248/230.1 |
| 5,857,685 | A * | 1/1999 | Phillips | A61M 5/1415 280/47.35 |
| 6,022,033 | A * | 2/2000 | Landesman | B62B 3/006 280/47.35 |
| 6,224,072 | B1 * | 5/2001 | Week | B62B 3/02 280/47.35 |
| 6,302,365 | B1 * | 10/2001 | Catanzarite | A47G 25/0614 248/339 |
| 6,601,860 | B2 * | 8/2003 | Potter | A61G 1/0212 280/47.35 |
| 7,865,983 | B2 * | 1/2011 | Newkirk | A61G 13/107 5/503.1 |

(Continued)

*Primary Examiner* — Jeffrey J Restifo
(74) *Attorney, Agent, or Firm* — Marin Patents LLC; Gustavo Marin (57) ABSTRACT

An apparatus for suspending one or more items is disclosed. The apparatus includes a vertical back plate, a vertical front plate, and a connector plate for connecting the vertical front plate to the vertical back plate. The apparatus further comprises an angulated base member attached to the vertical front plate at an obtuse angle. An arched hanging member for receiving one or more articles to be hanged is provided on the apparatus, the arched hanging member comprising a rounded ball end to avoid tears and perforations to the one or more suspended items.

10 Claims, 8 Drawing Sheets

(56) References Cited

U.S. PATENT DOCUMENTS

| | | | | |
|---|---|---|---|---|
| 7,992,833 B1* | 8/2011 | Goodman | .......... | A47G 25/0614 |
| | | | | 248/339 |
| 8,733,719 B2* | 5/2014 | Gaal | .................. | A61M 5/1415 |
| | | | | 280/292 |
| 8,875,770 B1* | 11/2014 | Martin | ..................... | A47K 3/38 |
| | | | | 160/124 |
| 9,936,828 B1* | 4/2018 | Adams, IV | ............... | A47G 1/17 |
| 10,786,407 B2* | 9/2020 | Ellis | ........................ | B60D 1/52 |
| 11,076,534 B1* | 8/2021 | Kacines | ............. | A47G 25/0614 |
| 2002/0101047 A1* | 8/2002 | Drury Chesser | ......... | B62B 3/10 |
| | | | | 280/47.35 |
| 2006/0022419 A1* | 2/2006 | Phillips, II | ................ | B62B 3/02 |
| | | | | 280/47.35 |
| 2007/0261330 A1* | 11/2007 | Liu | ........................ | A47H 13/04 |
| | | | | 52/235 |
| 2011/0010903 A1* | 1/2011 | Starbuck | .............. | A47G 29/083 |
| | | | | 24/716 |
| 2012/0291243 A1* | 11/2012 | Baines | ..................... | A47K 3/38 |
| | | | | 24/716 |
| 2016/0280243 A1* | 9/2016 | Devers | ................... | A47G 25/06 |
| 2017/0196380 A1* | 7/2017 | Chapman | .............. | E04B 2/7427 |
| 2018/0296018 A1* | 10/2018 | Baines | ................... | A47H 13/04 |
| 2020/0121111 A1* | 4/2020 | Engell | .................... | A47H 13/02 |
| 2020/0329897 A1* | 10/2020 | Wexler | ................. | A61G 7/0503 |
| 2021/0100409 A1* | 4/2021 | Grindley | ............ | A47K 10/3687 |
| 2021/0113404 A1* | 4/2021 | Caddell | ..................... | B62B 5/00 |
| 2021/0120994 A1* | 4/2021 | Gwen | ................... | A47H 13/01 |
| 2021/0179157 A1* | 6/2021 | Colling | .................... | B62B 3/04 |
| 2021/0244223 A1* | 8/2021 | Shepherd | ................ | A47H 1/06 |
| 2022/0304759 A1* | 9/2022 | Hansen | ................ | A61G 12/001 |

* cited by examiner

APPARATUS FOR SUSPENDING RADIO-OPAQUE CURTAINS

CROSS-REFERENCE TO RELATED APPLICATIONS

This application claims the benefit of and priority to U.S. provisional application 62/947,635 titled, "APPARATUS FOR SUSPENDING RADIO-OPAQUE CURTAINS" filed on Dec. 13, 2019. This application also claims the benefit of and priority to U.S. provisional application 62/988,542 titled, "APPARATUS FOR TRANSPORTING RADIO SHIELDING SYSTEMS" filed on Mar. 12, 2020, the entire specifications of which are incorporated herein by reference.

BACKGROUND OF THE INVENTION

Field of the Art

The disclosure relates to the field of radiation shielding systems, and more particularly to the field of suspending radio-opaque curtains.

Discussion of the State of the Art

Radiation such as X-rays or computed tomography (CT) scans are performed frequently in hospitals for health examination or treatment purposes. Medical radiation involves applying radiation such as X-rays, gamma-rays, beta rays, injecting radioactive isotopes into the body, or administering them orally to take imaging studies or treat various diseases. When the human body is exposed to radiation, cells can die, become malignant, or even mutate. If cells die, it can be harmful to tissues or organs. If DNA inside a cell is damaged, the cell can turn to cancer. If DNA damage occurs in a sperm or egg, it can lead to genetic problems such as congenital anomalies in the offspring.

Though in most hospitals, patients are given an explanation of the harms of radiation exposure and in some cases how much radiation they would be exposed to, little attention is paid to the effect of radiation on healthcare professionals. With an aging population and an increasing demand in radiation treatments, healthcare professionals are exposed to increased doses of radiation. Accordingly, healthcare professionals must wear manufactured protective clothing made of metal composites which are dense, warm and impervious, which causes discomfort and even physical pain among healthcare personnel. This reduces their performance and negatively affects the length of time they can work. Further, equipment in medical environments must not prevent sharp edges in order to mitigate glove perforations.

The problems noted above are exacerbated when safely storing and transporting heavy and cumbersome radio-opaque curtains from one location to another. Medical establishments must keep the integrity of the curtains when in storage or in movement so that they remain undamaged and fully functional.

What is needed in the art is a mechanism for easy and safe storage and transportation for radio-opaque curtains, aprons, and other radio-shielding systems. Specifically, when transporting when they can be exposed to dangerous items that can affect the efficacy and integrity of the shielding systems.

SUMMARY OF THE INVENTION

Accordingly, the inventor has conceived and reduced to practice, in a preferred embodiment of the invention, an apparatus for safely suspending and transporting radio-opaque curtains.

According to a preferred embodiment of the invention, an apparatus for safely suspending radio-opaque curtains comprises an angulated hook with an obtuse angle to separate a suspended curtain a pre-configured distance from a wall, a travel cart, and the like. The angulated hook having a ball end to mitigate perforation and damage prevent of the radio-opaque curtains or of other medical equipment (for example, an operator's glove). In some embodiments, a plurality of angulated hooks may be attached to a travel cart for mounting and transporting shielding systems into a substantially fixed position. Advantageously, the travel cart prevents curtains or aprons from moving side to side without lifting off and falling on floor to get lost or become a trip hazard. In a preferred embodiment, the disclosed angulated hook allows storage and transportation (for example, when coupled with a travel cart) of one or more shielding systems, curtains, aprons, or the like, when used in conjunction with other angulated hooks.

In a typical medical establishment, daily workflows of an exam room may be dedicated to radiation exams, or those that only perform radiation procedures intermittently. The ability to safely store and transport radiation protection equipment from room to room is typically needed as most establishments do not have dedicated shielding equipment in each examination room. Advantageously, an angulated hook with a ball end provides safety and convenience for storing radio-opaque curtains.

BRIEF DESCRIPTION OF THE DRAWING FIGURES

The accompanying drawings illustrate several embodiments of the invention and, together with the description, serve to explain the principles of the invention according to the embodiments. It will be appreciated by one skilled in the art that the particular embodiments illustrated in the drawings are merely exemplary and are not to be considered as limiting of the scope of the invention or the claims herein in any way.

DETAILED DESCRIPTION

The inventor has conceived, and reduced to practice, an apparatus for suspending one or more articles on a mounting surface.

One or more different inventions may be described in the present application. Further, for one or more of the inventions described herein, numerous alternative embodiments may be described; it should be appreciated that these are presented for illustrative purposes only and are not limiting of the inventions contained herein or the claims presented herein in any way. One or more of the inventions may be widely applicable to numerous embodiments, as may be readily apparent from the disclosure. In general, embodiments are described in sufficient detail to enable those skilled in the art to practice one or more of the inventions, and it should be appreciated that other embodiments may be utilized and that structural, logical, software, electrical and other changes may be made without departing from the scope of the particular inventions. Accordingly, one skilled in the art will recognize that one or more of the inventions may be practiced with various modifications and alterations. Particular features of one or more of the inventions described herein may be described with reference to one or more particular embodiments or figures that form a part of the present disclosure, and in which are shown, by way of illustration, specific embodiments of one or more of the inventions. It should be appreciated, however, that such features are not limited to usage in the one or more particular embodiments or figures with reference to which they are described. The present disclosure is neither a literal description of all embodiments of one or more of the inventions nor a listing of features of one or more of the inventions that must be present in all embodiments.

Headings of sections provided in this patent application and the title of this patent application are for convenience only and are not to be taken as limiting the disclosure in any way.

Figure 1:
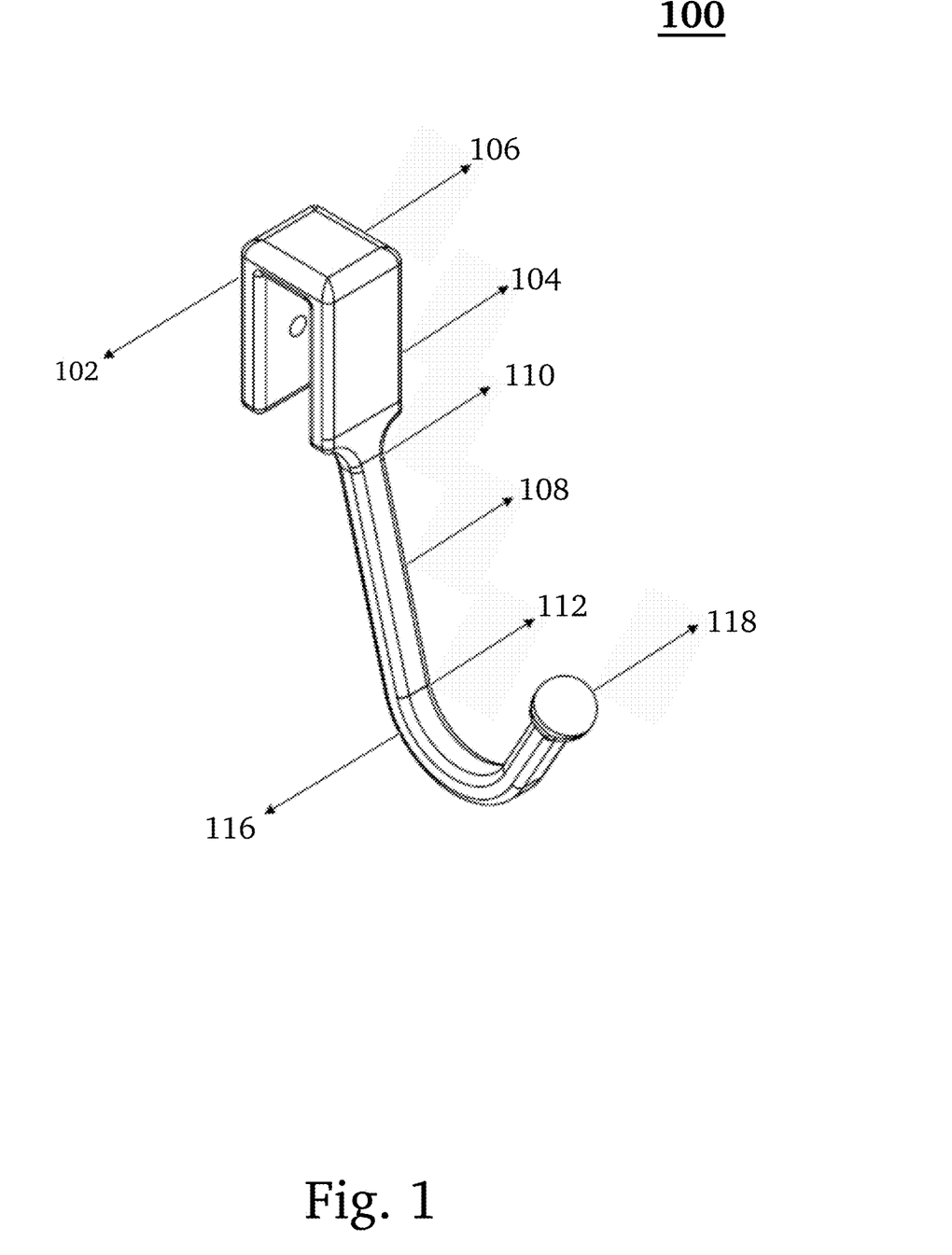
FIG. 1 illustrates a right-front isometric view of an apparatus for suspending one or more articles onto a mounting surface, according to a preferred embodiment of the present invention.

FIG. 1 is a right-front isometric view of an apparatus for suspending one or more articles onto a mounting surface, according to a preferred embodiment of the present invention. In a preferred embodiment, the one or more articles may comprise radio-opaque curtains, as used in the medical and diagnostic fields. The radio-opaque curtains may typically be used in the field of medicine as radiation protection shielding while working with medical imaging tests such as X-rays, magnetic resonance imaging (MRI) scans, computerized tomography (CT) scans, ultrasounds, and the like.

According to the embodiment, the apparatus for suspending radio-opaque curtains may be in the form of an angulated hook hanger 100 to receive one or more radio-opaque curtains. In an example, the one or more radio-opaque curtains may be suspended on a fixed position on a mounting surface, such as a wall (referring to FIG. 8), using hook hanger 100. In another example, the one or more radio-opaque walls may be suspended on a mounting surface using hook hanger 100 for transportation from one place to another, such as described in conjunction with FIG. 5.

Hook hanger 100 may comprise a vertical back plate 102 and a vertical front plate 104. In an embodiment, vertical back plate 102 and vertical front plate 104 may be, in a preferred embodiment, equal in dimensions (though in some embodiments they may be different lengths), and attached to one another in parallel. For instance, a top edge of vertical back plate 102 and a top edge of vertical front plate may be connected using a connected plate 106, as shown in FIG. 1. Further, hook hanger 100 may comprise an angulated base member 108 having a top edge 110 and a bottom edge 112. In an embodiment, angulated base member 108 may be integrally or fixedly attached to the bottom edge of the vertical front plate 104.

Further, in another embodiment, hook hanger 100 may comprise an arched hanging member 116 having a rounded ball end 118. The arched hanging member 116 may be operable to receive the one or more radio-opaque curtains, or other material to be hanged onto the mounting surface using hook hanger 100. Furthermore, rounded ball end 118 may ensure that perforations in the radio-opaque curtains or surgical gloves worn by medical professionals while hanging or retrieving the radio-opaque curtains from hook hanger 100, may be avoided. In an embodiment, angulated base member 108 may facilitate easier mounting of one or more shields or curtains to hook hanger 100.

Figure 2:
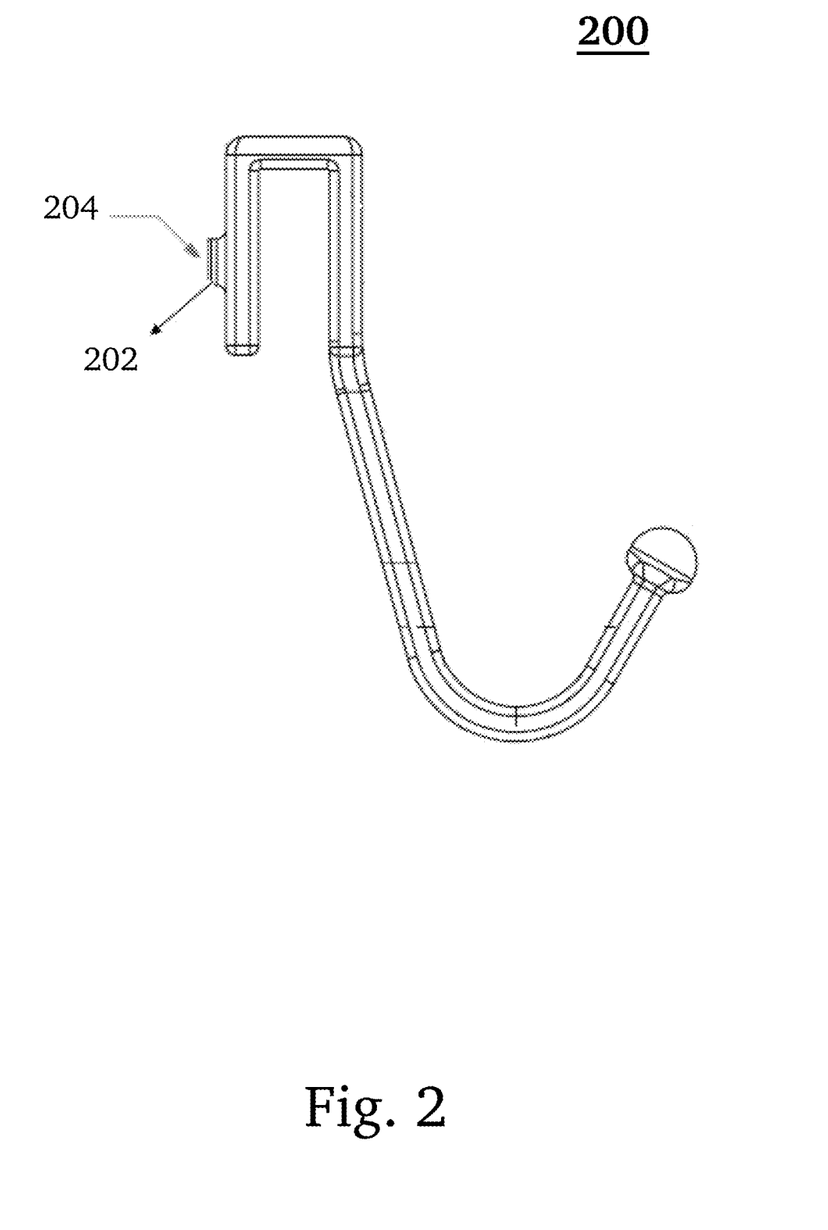
FIG. 2 illustrates a side view of an apparatus for suspending one or more items, according to a preferred embodiment of the present invention.

FIG. 2 illustrates a side view of an apparatus for suspending one or more items, according to a preferred embodiment of the invention. According to the embodiment, hook hanger 200 may comprise protruding member 202 detachably attached to a back surface of vertical back plate 102, as shown in the figure. In some embodiments, protruding member 202 may be integrally attached or machine formed. In a preferred embodiment, protruding member 202 may have a through hole 204 (shown in detail in FIG. 4), for receiving a screw or pin to attach hook hanger 200 on a mounting surface. In some embodiments, protruding member 202 may be operable affix hook hanger 200 onto a fixed position on the mounting surface via the screw or pin. In other embodiments, protruding member 202 may be operable to attach hook hanger 200 in a moveable position on the mounting surface, such that a position of hook hanger 200 may be changed on the mounting surface for easy retrieval of one or more objects hanging onto hook hanger 200. Further, such an arrangement may facilitate for hook hanger 200 to move from side to side on the mounting surface without detaching from the mounting surface. Further, a squared off base of hook hanger 200 may enable sturdiness while applying shields.

In some embodiments, through hole 204, when engaged with a screw or pin, may enable hook hanger 200 to mount the suspended one or more objects onto a rectangular rail with an indentation such that hook hanger 200 may move dynamically along an associated channel or groove within the rectangular rail, or be fixed in-place. The rectangular rail may be mounted on a fixed wall mount, a travel cart, or some other structure, described further in detail in conjunction with FIGS. 5-8.

Figure 3:
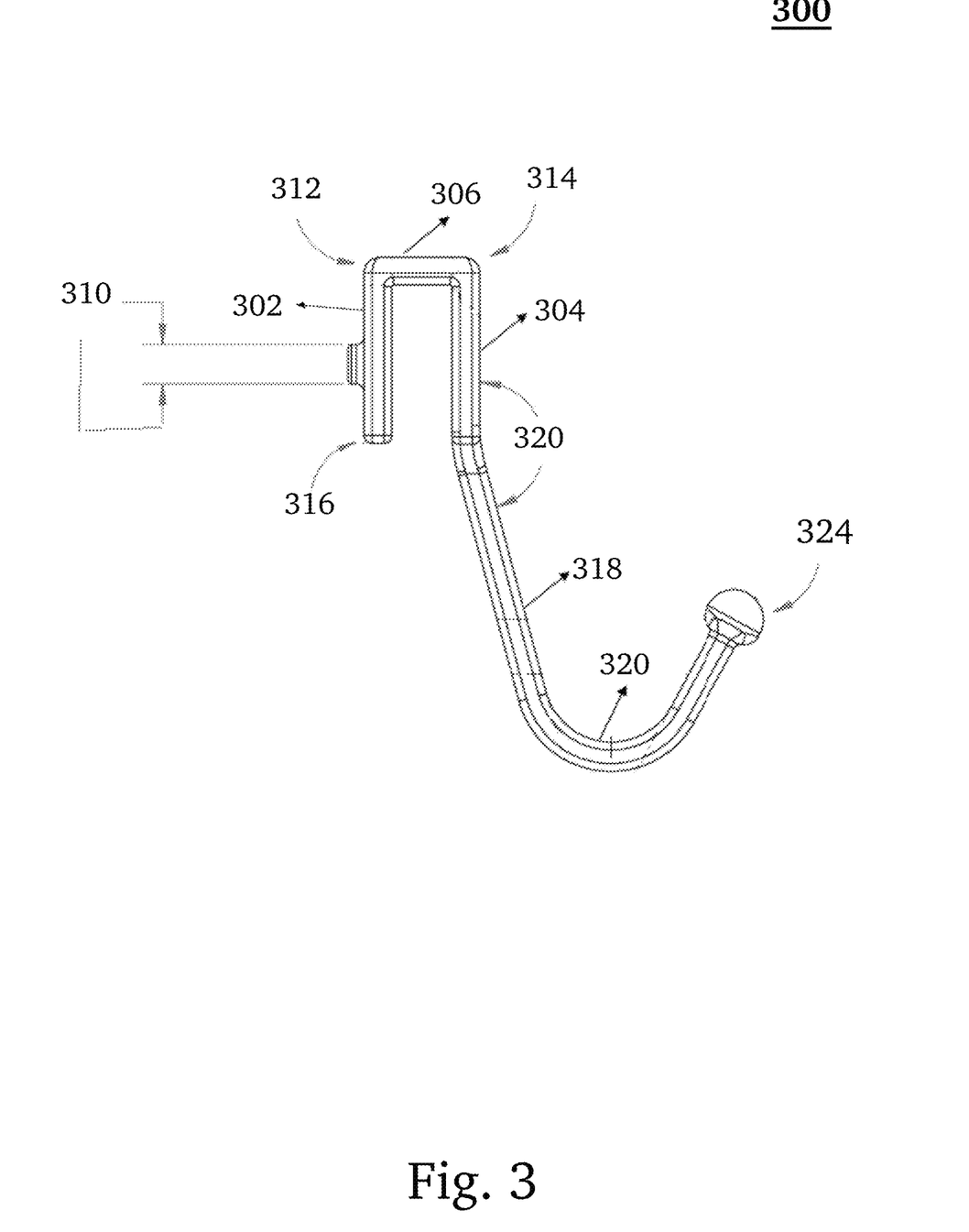
FIG. 3 illustrates another side view of an apparatus for suspending one or more objects, according to a preferred body of the invention.

FIG. 3 is another left elevational view of an apparatus for suspending one or more objects, according to a preferred body of the invention. According to the embodiment, the apparatus may be a hook hanger 300 for suspending radio-opaque curtains. Hook hanger 300 may comprise a vertical back plate 302, a vertical front plate 304, and a connecting plate 306, to attach vertical back plate 302 to vertical front plate 304. Hook hanger 300 may further comprise through hole 308 having a diameter 310 to receive a variety of standard screws and/or pins for affixation of hook hanger 300 on a mounting surface. In an example, the diameter 310 may range between 2 cm to 4 cm, with a preferred diameter 310 of 3.3 cm. In other embodiments, a different diameter may be used for diameter 310. Vertical back plate 302, vertical front plate 304, and connecting plate 306 of Hook hanger 300 may comprise rounded edges 312, 314, and 316 for mitigating tearing of surgical gloves and/or radio-opaque curtains, when suspending or removing radio-opaque curtains on and from hook hanger 300.

Hook hanger 300 may further comprise an angulated base member 318 detachably attached to a bottom edge of vertical front plate 304, such that there is an obtuse angle 320 between the vertical front plate 304 and angulated base member 318. In a preferred embodiment, obtuse angle 320 may range between 155 degrees to 175 degrees with a preferred obtuse angle 320 of 165 degrees. This arrangement may advantageously allow for spacing an engaged radio-opaque curtain at a pre-defined distance from a mounting surface such as a wall or travel cart when, for example, hook hanger 300 is used for suspending radio-opaque curtains to the mounting surface.

Hook hanger 300 may further comprise of an arching member 322 attached to a bottom end of angulated base member 318. Arching member 322 may comprise a rounded ball end 324 that may advantageously avoid tears and perforations in gloves, clothes, and the mounted radio-opaque curtains, when medical professionals use hook hanger 300 to store radio-opaque curtains onto a mounting surface. Further, rounded ball end 324 may prevent slippage of a suspended curtain when in transport (for example by preventing the curtain from sliding off in a situation where the cart was bumped r jolted.)

Figure 4:
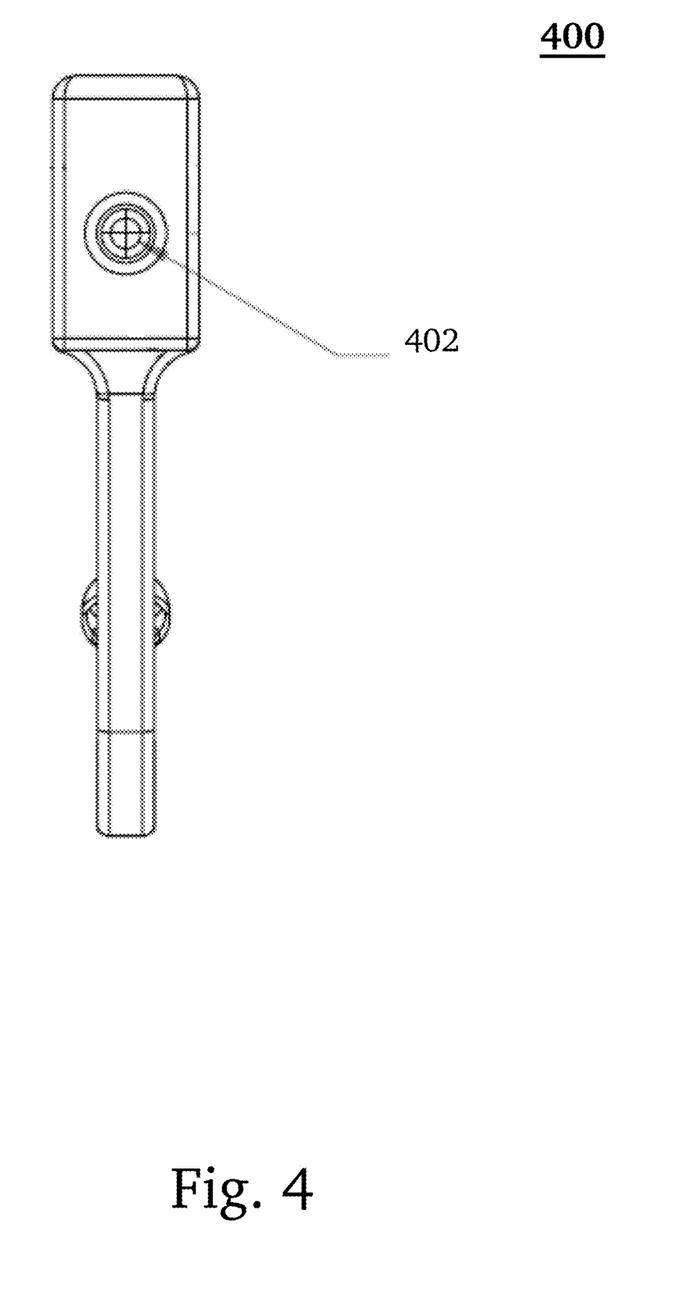
FIG. 4 illustrates a back elevational view of an apparatus for suspending one or more objects according to a preferred body of the invention.

FIG. 4 is a back elevational view of an apparatus for suspending one or more objects, according to a preferred body of the invention. According to the embodiment, the apparatus may be in the form of a hook hanger 400 comprising of a through hole 402 on a vertical back plate 404. The through hole 402 may present a threaded (or in some embodiments, unthreaded) hole for accepting a screw or pin for securing the apparatus to another structure (for example, a support bar).

Figure 5:
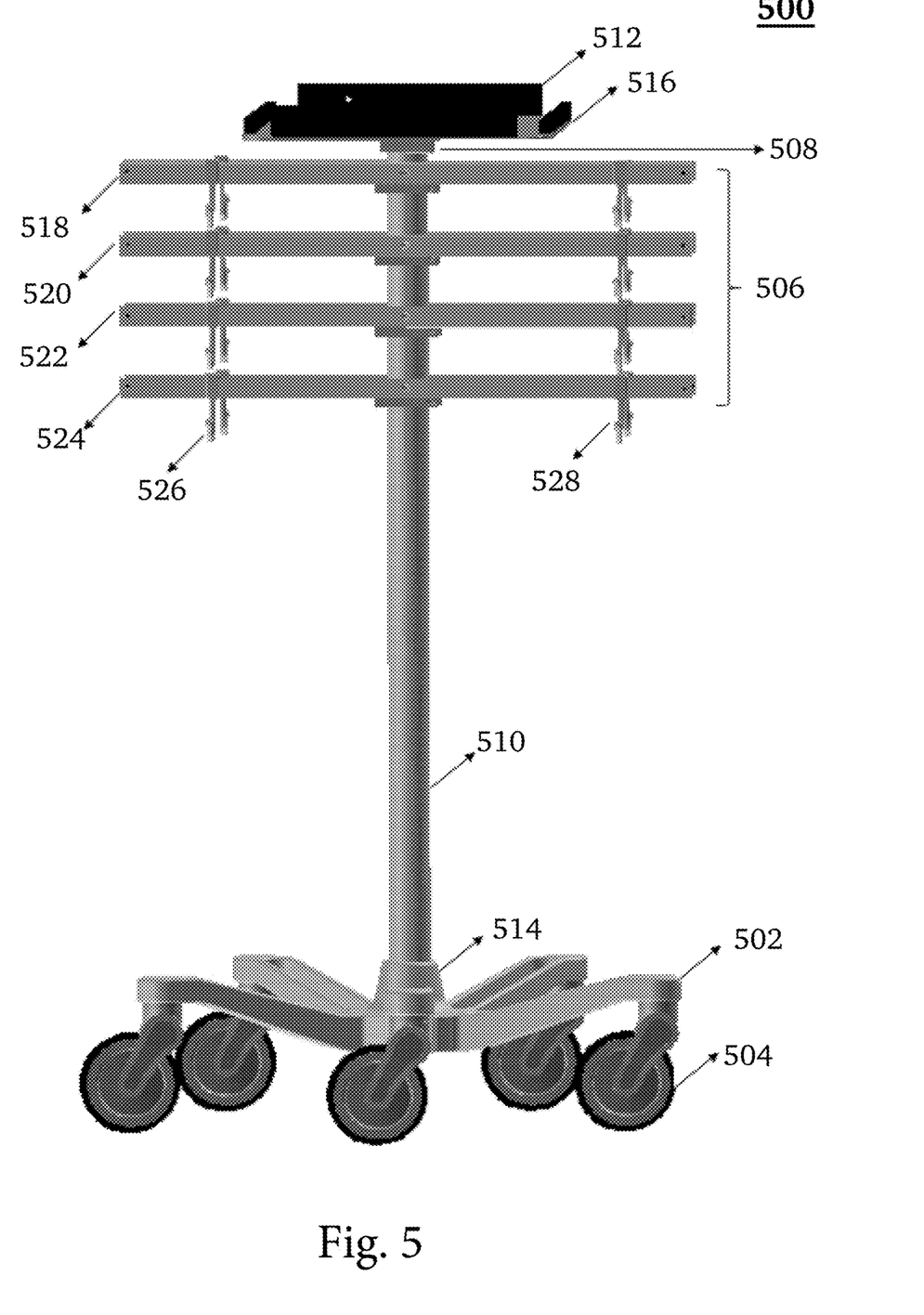
FIG. 5 illustrates a front view of an apparatus for suspending one or more objects, according to a preferred body of the invention.

FIG. 5 is a front view of an apparatus for suspending radio-opaque curtains, according to a preferred body of the invention. The apparatus may take the form of a transportation trolley 500, having a base portion 502 comprising of a plurality of wheels 504. Transportation trolley 500 may further comprise a supporting frame 506 attached to the base portion 502 through a first end 508 of a vertical connecting member 510; and a holding tray 512. Base portion 4 may be attached to a second end 514 of vertical connecting member 510. Further, a handle 516 may be attached to the holding tray 512, that may be operable to manoeuvre the transportation trolley using the plurality of wheels 504.

In an embodiment, supporting frame 506 may comprise of at least one mounting rail, such as mounting rails 518, 520, 522, and 524 that may support a plurality of hook hangers (referring to FIGS. 1-4), as represented by hook hangers 526 and 528. The plurality of hooks may in turn support one or more radiation shields, aprons, or other shielding apparel to be mounted on transportation trolley 500 for easy transportation. The transportation trolley 500, via an included mounting rail, may also be additionally operable to store one or more of shield support blocks (referring to USPTO patent application Ser. No. 16/172,764 incorporated herein by reference). In a preferred embodiment, there may be one or more handles, represented by handles 542 and 544, to manoeuvre transportation trolley 500 using the plurality of wheels 504.

In some embodiments, where shielding apparel may vary in size, the plurality of hooks 526-540 may provide a dynamic range of movement to accommodate the different sizes. In a preferred embodiment, the plurality of hooks 526-540 may be affixed in a manner such as to not allow the plurality of hooks to accidently fall off, thereby mitigating safety concerns (such as a trip hazard).

Figure 6:
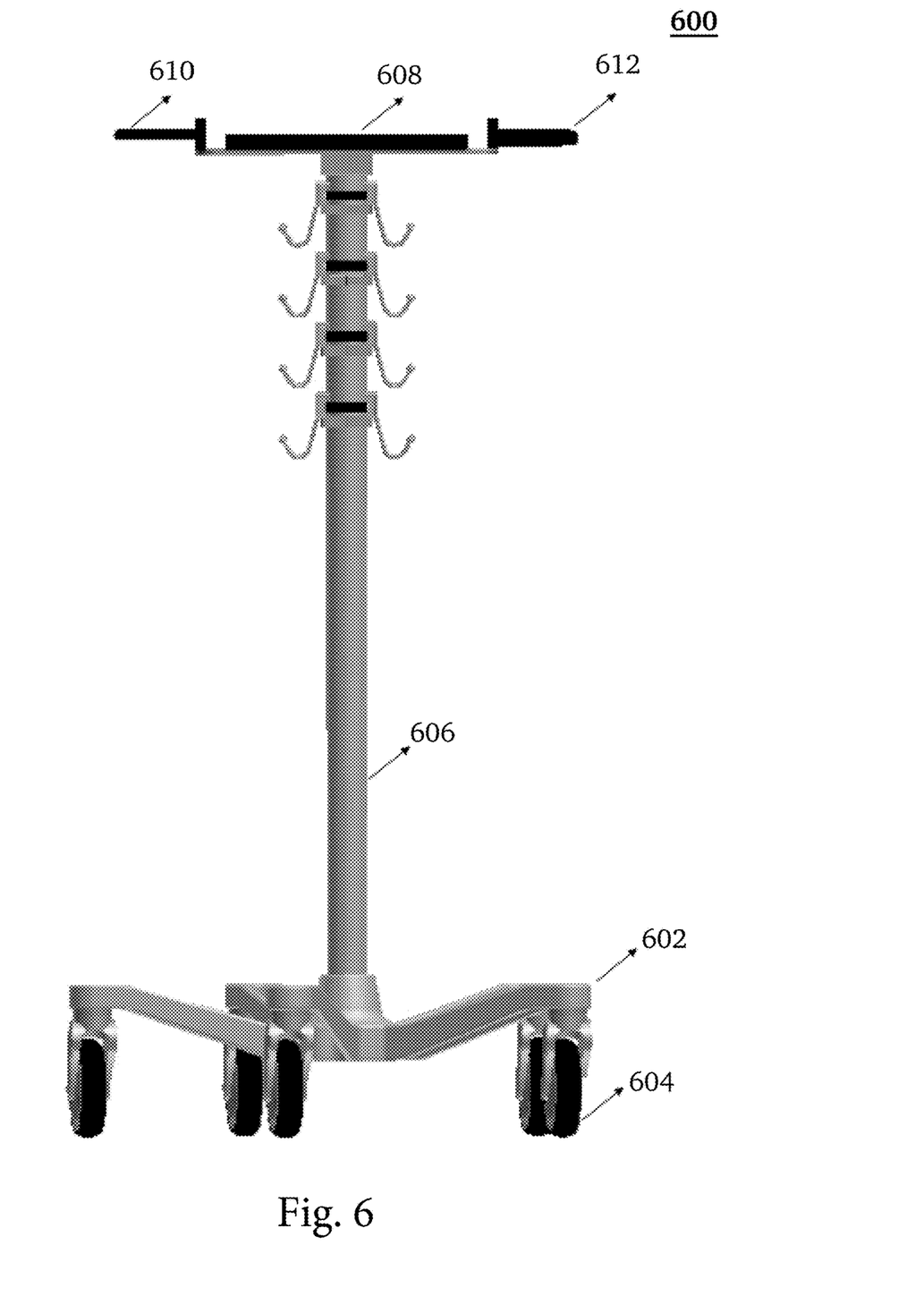
FIG. 6 illustrates a bottom-up view of an apparatus for suspending one or more objects, according to a preferred embodiment of the invention.

FIG. 6 is a bottom-up view of an apparatus for transporting one or more objects, according to a preferred embodiment of the invention. According to the embodiment, the apparatus may take form of a transportation trolley 600, having a base portion 602, a plurality of wheels 604, a vertical connecting member 606, a supporting frame (not shown), a holding tray 608, and handles 610 and 612.

In some embodiments, the plurality of wheels 604 may comprise of single, double, or compound wheels that may be attached to the base portion 602 to enable the transportation trolley 600 to be moved. In some embodiments, a swivel may create operability for the plurality of wheels 604 to incorporate a 360° turning movement. In some embodiments, a small amount of offset distance between a center axis of the vertical connecting member 606 and a center axis of each wheel may be implemented such that when a wheel is moved and said wheel is not moving in a desired direction, the offset may cause the plurality of wheels 604 to rotate around the axis of the vertical connecting member 606 to follow the desired direction of movement, using handles 612 and 614. The plurality of wheels 604 may be variable in size, and are commonly made of rubber, plastic, nylon, aluminum, or stainless steel.

Figure 7:
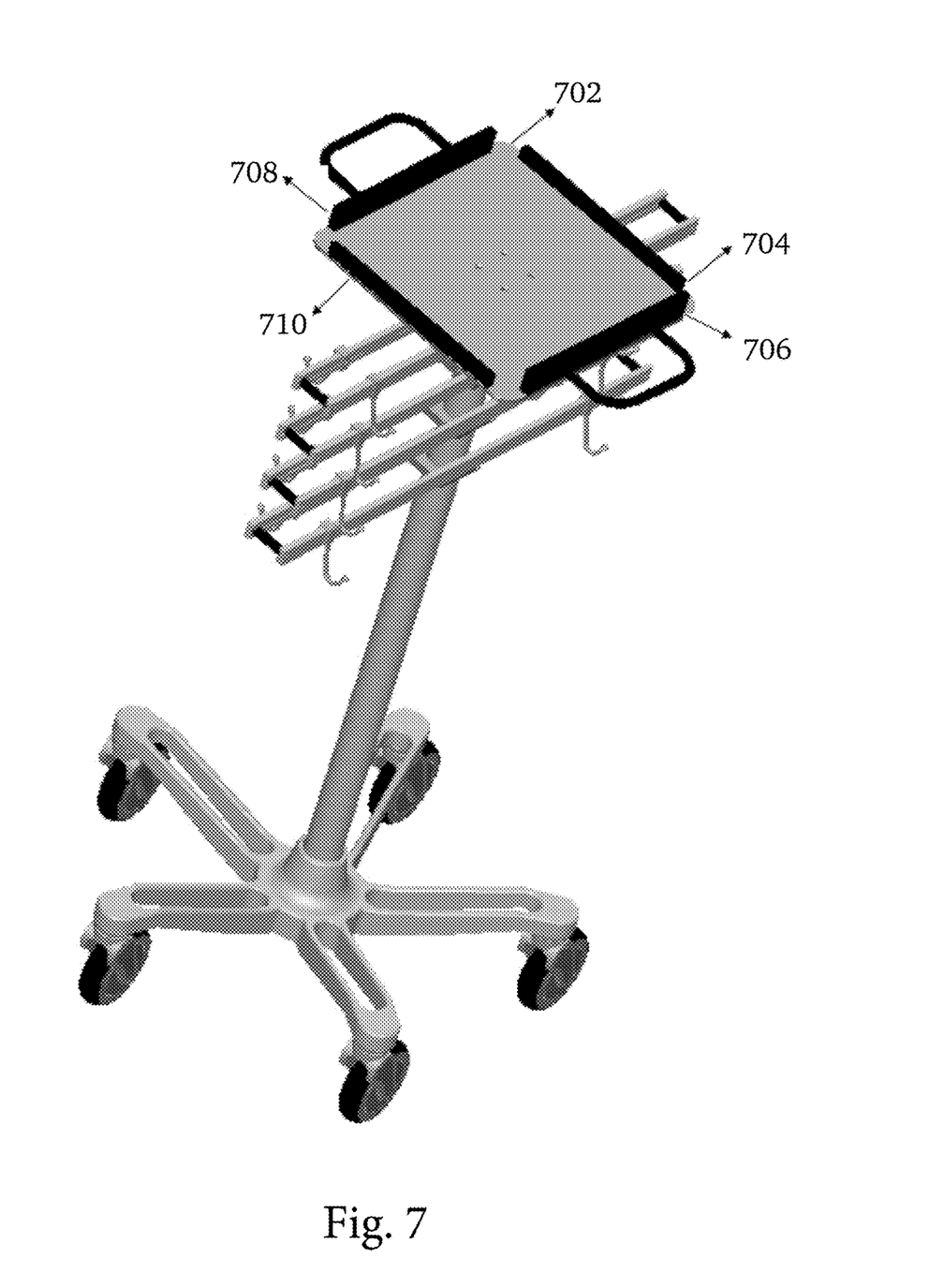
FIG. 7 is a top-down view of an apparatus for transporting one or more objects, according to a preferred body of the invention.

FIG. 7 is a top-down view of an apparatus for transporting one or more objects, according to a preferred body of the invention. The apparatus may take form of a transportation trolley 700. Transportation trolley 700 may comprise a flat surface 702 at a top end, such that flat surface 702 may be operable as a holding tray to hold and store one or more items, for example, lab coats, aprons, radio-opaque curtains, etc. It may be appreciated by one with ordinary skill in the art that the specific arrangement or configuration may vary, for example, the flat surface 702 may also be attached at a bottom end of transportation trolley 700. In some embodiments, instead of flat surface 702, transportation trolley 700 may comprise a holding area of a different shape, for example, a rounded basket. In some embodiments, flat surface 702 may comprise one or more raised sides/edges, represented by edges 704-710, whereby at least one such edge may be collapsible, for example, to allow for easier cleaning of unwanted dust or debris.

Figure 8:
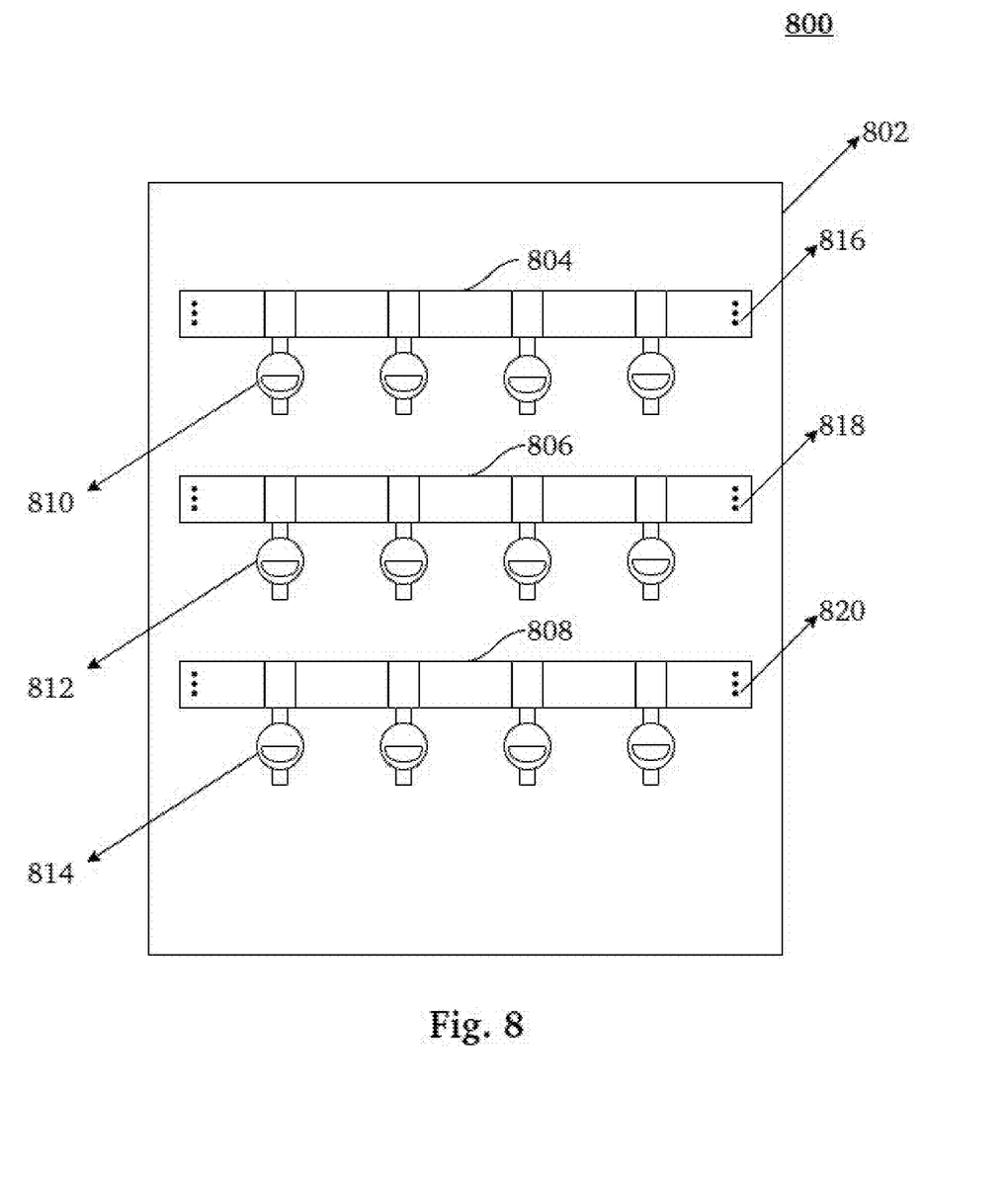
FIG. 8 is a front view of a mounting surface for hanging one or more items, according to a preferred body of the invention.

FIG. 8 is a front view of a mounting surface for hanging one or more items, according to a preferred body of the invention. According to the embodiment, storage rack 800 comprises a supporting frame 802. In some embodiments, frame 802 may be a back plate. Storage rack 800 may further comprise one or more mounting rails 804, 806, and 808. Each mounting rail, may comprise of a plurality of hook hangers, as represented by hook hangers 810, 812, and 814. The plurality of hook hangers may be attached to the mounting rails, as described in detail in FIGS. 1-4. Further, each mounting rail may be attached to a fixed position on supporting frame 802 by means of a plurality of screws, as represented by screws 816, 818, and 820. In a preferred embodiment mounting rails 804, 806, and 808 may each comprise a channel or groove for receiving a screw or pin (as described in FIG. 2)

The skilled person will be aware of a range of possible modifications of the various embodiments described above.

What is claimed is:

1. A hook hanger comprising:
   a vertical back plate;
   a vertical front plate, wherein the vertical front plate and the vertical back plate are equal in length;
   a connector plate for connecting a top edge of the vertical front plate to a top edge of the vertical back plate;
   an angulated base member comprising a top edge and a bottom edge, wherein the top edge of the angulated base member is attached to a bottom surface of the vertical front plate at an obtuse angle; and
   an arched hanging member for receiving one or more articles to be hanged on the hook hanger, the arched hanging member comprising a top edge and ball end, wherein the top edge of the arched hanging member is attached to the bottom edge of the angulated base member.

2. The hook hanger of claim 1, wherein the angulated base member is connected to the second vertical front plate at an obtuse angle having a range between 155 degrees and 175 degrees.

3. The hook hanger of claim 2, wherein the angulated base member is connected to the second vertical front plate at an obtuse angle of 165 degrees.

4. The hook hanger of claim 1, further comprising a protruding member detachably attached to a back portion of the first vertical back plate, wherein the protruding member is operable to secure the hook hanger to a fixed position on a mounting surface.

5. The hook hanger of claim 4, wherein the protruding member comprises a through hole for receiving one of a screw and a pin to secure the hook hanger to the fixed position on the mounting surface.

6. The hook hanger of claim 5, wherein the mounting surface is one of a wall, a storage rack, a mounting rail, and a transportation trolley.

7. The hook hanger of claim 6, wherein the transportation trolley comprises:
  a base portion comprising of plurality of wheels;
  a supporting frame attached to the base portion through a first end of a vertical connecting member, the supporting frame comprising at least one mounting rail;
  a holding tray attached to a second end of the vertical connecting member; and
  a handle attached to the holding tray and operable to manoeuvre the transportation trolley using the plurality of wheels;
  wherein the at least one mounting rail is operable to receive one or more hook hangers.

8. The hook hanger of claim 7, wherein the at least one mounting rail comprises a channel for receiving a screw removably attached to the one or more hook hangers.

9. The hook hanger of claim 6, wherein the storage rack further comprises:
  a supporting frame; and
  a plurality of parallel mounting rails detachably attached to the supporting frame, each mounting rail attached to the supporting frame using a plurality of screws;
  wherein each mounting rail of the plurality of parallel mounting rails is operable to receive one or more hook hangers.

10. The hook hanger of claim 9, wherein each mounting rail, of the plurality of parallel mounting rails, comprises a channel for receiving a screw removably attached to the one or more hook hangers.

* * * * *